US008596265B2

(12) United States Patent
Meyer et al.

(10) Patent No.: US 8,596,265 B2
(45) Date of Patent: Dec. 3, 2013

(54) MODULAR AEROSOL DELIVERY SYSTEM

(75) Inventors: Adam Meyer, London (CA); James Schmidt, London (CA); Chris Dobson, Sebringville (CA); Daniel Engelbreth, London (CA)

(73) Assignee: Trudell Medical International, London (CA)

( * ) Notice: Subject to any disclaimer, the term of this patent is extended or adjusted under 35 U.S.C. 154(b) by 1018 days.

(21) Appl. No.: 12/603,700

(22) Filed: Oct. 22, 2009

(65) Prior Publication Data

US 2010/0101570 A1  Apr. 29, 2010

Related U.S. Application Data

(60) Provisional application No. 61/107,435, filed on Oct. 22, 2008.

(51) Int. Cl.
*A61M 11/00* (2006.01)
*A61M 15/00* (2006.01)
*A61M 16/10* (2006.01)

(52) U.S. Cl.
USPC .................................. 128/200.23; 128/203.12

(58) Field of Classification Search
USPC ............. 128/200.11, 200.23, 200.24, 203.12; 128/203.15, 203.16, 204.18, 205.23; 222/23, 24, 29, 30, 44, 635
See application file for complete search history.

(56) References Cited

U.S. PATENT DOCUMENTS

| 165,054 A | 6/1875 | Baldwin |
| 498,851 A | 6/1893 | Jones |
| 1,219,858 A | 3/1917 | Patterson |
| 2,455,962 A | 12/1948 | Wheeler et al. |

(Continued)

FOREIGN PATENT DOCUMENTS

| AU | 598250 B2 | 6/1990 |
| CA | 535 518 A | 1/1957 |

(Continued)

OTHER PUBLICATIONS

U.S. Department of Health and Human Services, Food and Drug Administration, Center for Drug Evaluation and Research (CDER)—Clinical, "Guidance for Industry: Integration of Dose-Counting Mechanisms into MDI Drug Products—Draft Guidance," dated Nov. 2001, 6 pages.

(Continued)

*Primary Examiner* — Justine Yu
*Assistant Examiner* — Valerie L Skorupa
(74) *Attorney, Agent, or Firm* — Brinks Gilson & Lione

(57) ABSTRACT

In a modular medicament delivery system, a dispenser housing has a support block with a well and an orifice communicating with the well. A first container assembly includes a valve stem shaped to be received by the well in the support block. The first container assembly has a first exterior shape. A second container assembly includes a valve stem shaped to be received by the well in the support block. The second container assembly has a second exterior shape that is different than the first exterior shape. An insert member is adapted for mounting to the dispenser housing in the cavity and defines an interior space shaped to receive the second exterior shape of the second container. Methods of assembling the system, a system kit and a device are also provided. A medication delivery device includes first and second end pieces and a collapsible chamber disposed therebetween.

41 Claims, 12 Drawing Sheets

(56) References Cited

U.S. PATENT DOCUMENTS

| | | |
|---|---|---|
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,841,190 A | 7/1958 | Sheck |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,074,831 A | 2/1978 | Roach |
| 4,078,661 A | 3/1978 | Thomas |
| 4,094,408 A | 6/1978 | Ford |
| 4,117,952 A | 10/1978 | Grimes |
| 4,162,746 A | 7/1979 | Anderson et al. |
| 4,164,301 A | 8/1979 | Thayer |
| 4,171,753 A | 10/1979 | Vreede |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,627,432 A | 12/1986 | Newell et al. |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newell-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,934,358 A | 6/1990 | Nilsson et al. |
| 4,934,568 A | 6/1990 | Fuchs |
| 4,938,210 A | 7/1990 | Shene |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,056,454 A | 10/1991 | Turner |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,226,539 A | 7/1993 | Cheng |

(56) References Cited

U.S. PATENT DOCUMENTS

| | | | |
|---|---|---|---|
| 5,227,764 A | 7/1993 | Umemoto | |
| 5,228,586 A | 7/1993 | Fuchs | |
| 5,242,067 A | 9/1993 | Garby et al. | |
| 5,243,970 A | 9/1993 | Amrosio et al. | |
| 5,261,548 A | 11/1993 | Barker et al. | |
| 5,263,475 A | 11/1993 | Altermatt et al. | |
| 5,284,133 A | 2/1994 | Burns et al. | |
| 5,289,946 A | 3/1994 | Fuchs | |
| 5,297,543 A * | 3/1994 | Larson et al. | 128/200.23 |
| 5,299,701 A | 4/1994 | Barker et al. | |
| 5,300,042 A | 4/1994 | Kossoff et al. | |
| 5,301,873 A | 4/1994 | Burke et al. | |
| 5,318,016 A | 6/1994 | Mecikalski | |
| 5,328,597 A | 7/1994 | Boldt, Jr. et al. | |
| 5,331,953 A | 7/1994 | Andersson et al. | |
| 5,335,823 A | 8/1994 | Fuchs et al. | |
| 5,349,944 A | 9/1994 | Chippendale et al. | |
| 5,349,945 A * | 9/1994 | Wass et al. | 128/200.23 |
| 5,356,012 A | 10/1994 | Tang et al. | |
| 5,356,406 A | 10/1994 | Schraga | |
| 5,357,946 A * | 10/1994 | Kee et al. | 128/200.24 |
| 5,363,842 A | 11/1994 | Mishelevich et al. | |
| 5,370,267 A | 12/1994 | Schroeder | |
| 5,378,233 A | 1/1995 | Haber et al. | |
| 5,379,804 A | 1/1995 | Dunn et al. | |
| 5,382,243 A | 1/1995 | Mulholland | |
| RE34,847 E | 2/1995 | Muderlak et al. | |
| 5,388,572 A | 2/1995 | Mulhauser et al. | |
| 5,392,768 A | 2/1995 | Johansson et al. | |
| 5,394,866 A | 3/1995 | Ritson et al. | |
| 5,397,028 A | 3/1995 | Jesadanont | |
| 5,411,173 A | 5/1995 | Weinstein | |
| 5,421,482 A | 6/1995 | Garby et al. | |
| 5,437,270 A | 8/1995 | Braithwaite | |
| 5,447,150 A | 9/1995 | Bacon | |
| 5,448,042 A | 9/1995 | Robinson et al. | |
| 5,468,233 A | 11/1995 | Schraga | |
| 5,474,058 A * | 12/1995 | Lix | 128/200.18 |
| 5,482,030 A | 1/1996 | Klein | |
| 5,482,163 A | 1/1996 | Hoffman | |
| 5,498,243 A | 3/1996 | Vallelunga et al. | |
| 5,505,192 A | 4/1996 | Samiotes et al. | |
| 5,505,195 A | 4/1996 | Wolf et al. | |
| 5,509,905 A | 4/1996 | Michel | |
| 5,519,197 A | 5/1996 | Robinson et al. | |
| 5,520,166 A | 5/1996 | Ritson et al. | |
| 5,522,378 A | 6/1996 | Ritson et al. | |
| 5,524,613 A | 6/1996 | Haber et al. | |
| 5,544,647 A | 8/1996 | Jewett et al. | |
| 5,549,101 A | 8/1996 | Trofast et al. | |
| 5,564,414 A | 10/1996 | Walker et al. | |
| 5,574,268 A | 11/1996 | Herman et al. | |
| 5,577,335 A | 11/1996 | Tucker | |
| 5,584,815 A | 12/1996 | Pawelka et al. | |
| 5,611,444 A | 3/1997 | Garby et al. | |
| 5,617,844 A * | 4/1997 | King | 128/200.18 |
| 5,622,163 A | 4/1997 | Jewett et al. | |
| 5,625,334 A | 4/1997 | Compton | |
| 5,625,659 A | 4/1997 | Sears | |
| 5,626,566 A | 5/1997 | Petersen et al. | |
| 5,638,970 A | 6/1997 | Garby et al. | |
| 5,657,748 A | 8/1997 | Braithwaite | |
| 5,676,129 A | 10/1997 | Rocci, Jr. et al. | |
| 5,687,710 A | 11/1997 | Ambrosio et al. | |
| 5,692,492 A | 12/1997 | Bruna et al. | |
| 5,694,882 A | 12/1997 | Marshall | |
| 5,697,916 A | 12/1997 | Schraga | |
| 5,701,886 A | 12/1997 | Ryatt | |
| 5,718,355 A | 2/1998 | Garby et al. | |
| 5,724,957 A | 3/1998 | Rubsamen et al. | |
| 5,732,836 A | 3/1998 | Barker et al. | |
| 5,740,792 A | 4/1998 | Ashley et al. | |
| 5,758,638 A | 6/1998 | Kreamer | |
| 5,772,074 A | 6/1998 | Dial et al. | |
| 5,794,612 A | 8/1998 | Wachter et al. | |
| 5,799,651 A | 9/1998 | Garby et al. | |
| 5,803,283 A | 9/1998 | Barker et al. | |
| 5,809,996 A | 9/1998 | Alldredge | |
| 5,809,997 A | 9/1998 | Wolf | |
| 5,826,571 A | 10/1998 | Casper et al. | |
| 5,829,434 A | 11/1998 | Ambrosio et al. | |
| 5,845,777 A | 12/1998 | Najmi | |
| 5,852,590 A | 12/1998 | de la Huerga | |
| 5,871,007 A | 2/1999 | Clark, Jr. | |
| 5,873,995 A | 2/1999 | Huang et al. | |
| 5,882,507 A | 3/1999 | Tanner et al. | |
| 5,896,855 A | 4/1999 | Hobbs | |
| 5,896,990 A | 4/1999 | Barzana | |
| 5,899,201 A | 5/1999 | Schultz et al. | |
| 5,904,139 A | 5/1999 | Hauser | |
| 5,957,896 A | 9/1999 | Bendek et al. | |
| 5,961,495 A | 10/1999 | Walters et al. | |
| 5,988,496 A | 11/1999 | Bruna | |
| 6,000,159 A | 12/1999 | Hornung | |
| 6,001,082 A | 12/1999 | Dair et al. | |
| 6,012,450 A | 1/2000 | Rubsamen | |
| 6,014,972 A * | 1/2000 | Sladek | 128/203.12 |
| 6,029,659 A | 2/2000 | O'Connor | |
| 6,059,133 A | 5/2000 | Lai | |
| 6,062,214 A | 5/2000 | Howlett | |
| 6,076,521 A | 6/2000 | Lindahl et al. | |
| 6,082,358 A | 7/2000 | Scarrott et al. | |
| 6,089,180 A | 7/2000 | Nichols, Jr. | |
| 6,096,010 A | 8/2000 | Walters et al. | |
| 6,119,684 A | 9/2000 | Nohl et al. | |
| 6,138,669 A | 10/2000 | Rocci, Jr. et al. | |
| 6,142,339 A | 11/2000 | Blacker et al. | |
| 6,148,815 A | 11/2000 | Wolf | |
| 6,149,054 A | 11/2000 | Cirrillo | |
| 6,155,251 A | 12/2000 | Hauser | |
| 6,161,724 A | 12/2000 | Blacker et al. | |
| 6,164,494 A | 12/2000 | Marelli | |
| 6,182,655 B1 | 2/2001 | Keller et al. | |
| 6,186,364 B1 | 2/2001 | Dobbs | |
| 6,202,642 B1 | 3/2001 | McKinnon et al. | |
| 6,221,053 B1 | 4/2001 | Walters et al. | |
| 6,223,744 B1 | 5/2001 | Garon | |
| 6,234,168 B1 | 5/2001 | Bruna | |
| 6,283,365 B1 | 9/2001 | Bason | |
| 6,318,600 B1 * | 11/2001 | Winnett et al. | 222/173 |
| 6,328,037 B1 | 12/2001 | Scarrott et al. | |
| 6,336,453 B1 | 1/2002 | Scarrott et al. | |
| 6,360,739 B1 | 3/2002 | Rand et al. | |
| 6,405,727 B1 | 6/2002 | MacMichael et al. | |
| 6,415,785 B1 | 7/2002 | Stage | |
| 6,425,392 B1 | 7/2002 | Sosiak | |
| 6,431,168 B1 | 8/2002 | Rand et al. | |
| 6,435,372 B1 | 8/2002 | Blacker et al. | |
| 6,446,627 B1 | 9/2002 | Bowman et al. | |
| 6,463,929 B1 | 10/2002 | Scheuch et al. | |
| 6,474,331 B1 | 11/2002 | Rand et al. | |
| 6,481,438 B1 | 11/2002 | Gallem et al. | |
| 6,484,717 B1 | 11/2002 | Dagsland et al. | |
| 6,516,799 B1 | 2/2003 | Greenwood et al. | |
| 6,529,446 B1 | 3/2003 | de la Huerga | |
| 6,561,384 B2 | 5/2003 | Blacker et al. | |
| 6,601,582 B2 | 8/2003 | Rand et al. | |
| 6,615,827 B2 | 9/2003 | Greenwood et al. | |
| 6,659,307 B1 | 12/2003 | Stradella | |
| 6,679,251 B1 | 1/2004 | Gallem et al. | |
| 6,701,917 B2 | 3/2004 | O'Leary | |
| 6,718,972 B2 | 4/2004 | O'Leary | |
| 6,729,330 B2 | 5/2004 | Scarrott et al. | |
| 6,752,153 B1 | 6/2004 | Eckert | |
| 6,761,161 B2 | 7/2004 | Scarrott et al. | |
| 6,766,799 B2 | 7/2004 | Edwards et al. | |
| 6,769,601 B2 | 8/2004 | Haikarainen et al. | |
| 6,907,876 B1 | 6/2005 | Clark et al. | |
| 6,938,796 B2 | 9/2005 | Blacker et al. | |
| 6,997,349 B2 | 2/2006 | Blacker et al. | |
| 7,137,391 B2 | 11/2006 | Bruna | |
| 7,143,764 B1 | 12/2006 | Dagsland et al. | |
| 7,143,908 B2 | 12/2006 | Blacker et al. | |
| 7,156,258 B2 | 1/2007 | Eckert | |

(56) References Cited

U.S. PATENT DOCUMENTS

| | | | |
|---|---|---|---|
| 7,207,329 B2* | 4/2007 | Bowden | 128/203.12 |
| 7,360,537 B2 | 4/2008 | Snyder et al. | |
| 7,407,066 B2 | 8/2008 | Ouyang et al. | |
| 7,555,995 B1 | 7/2009 | Stump et al. | |
| 7,575,130 B2 | 8/2009 | Blacker et al. | |
| 7,793,798 B2 | 9/2010 | Stradella et al. | |
| 7,984,826 B2 | 7/2011 | Blacker et al. | |
| 2002/0000225 A1 | 1/2002 | Schuler et al. | |
| 2002/0104531 A1* | 8/2002 | Malone | 128/200.23 |
| 2002/0153005 A1 | 10/2002 | Scarrott et al. | |
| 2003/0183225 A1 | 10/2003 | Knudsen | |
| 2003/0200964 A1 | 10/2003 | Blakley et al. | |
| 2003/0205227 A1 | 11/2003 | Hodson | |
| 2003/0209239 A1* | 11/2003 | Rand et al. | 128/200.23 |
| 2004/0065326 A1 | 4/2004 | MacMichael et al. | |
| 2004/0069301 A1 | 4/2004 | Bacon | |
| 2004/0089296 A1 | 5/2004 | Bowden | |
| 2004/0094147 A1 | 5/2004 | Schyra et al. | |
| 2004/0144798 A1 | 7/2004 | Ouyang et al. | |
| 2004/0149772 A1 | 8/2004 | Ouyang | |
| 2004/0149773 A1 | 8/2004 | Ouyang et al. | |
| 2004/0221840 A1 | 11/2004 | Stockman-Lamb | |
| 2004/0255935 A1 | 12/2004 | Bruna | |
| 2004/0255936 A1 | 12/2004 | Urbanus | |
| 2005/0011515 A1 | 1/2005 | Lee et al. | |
| 2005/0039746 A1 | 2/2005 | Grychowski et al. | |
| 2005/0056276 A1 | 3/2005 | Schuler et al. | |
| 2005/0268905 A1 | 12/2005 | Rasmussen et al. | |
| 2005/0284471 A1 | 12/2005 | Bruna | |
| 2006/0060192 A1* | 3/2006 | Lu et al. | 128/200.23 |
| 2006/0254579 A1* | 11/2006 | Grychowski et al. | 128/200.22 |
| 2006/0254581 A1 | 11/2006 | Genova et al. | |
| 2006/0260608 A1* | 11/2006 | Armstrong et al. | 128/200.23 |
| 2007/0056581 A1 | 3/2007 | Obuz | |
| 2007/0074718 A1* | 4/2007 | Austin | 128/200.23 |
| 2007/0084462 A1 | 4/2007 | Allen | |
| 2007/0277817 A1 | 12/2007 | Innocenzi | |
| 2008/0066741 A1* | 3/2008 | LeMahieu et al. | 128/200.21 |
| 2008/0264412 A1 | 10/2008 | Meyer et al. | |

FOREIGN PATENT DOCUMENTS

| | | |
|---|---|---|
| CA | 2 152 088 A | 7/1994 |
| CA | 2 181 789 C | 6/1996 |
| CA | 2 486 892 A1 | 12/1998 |
| CA | 2 315 777 A1 | 7/1999 |
| CA | 2 331 179 A1 | 11/1999 |
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| DE | 6 603 758 U | 7/1969 |
| DE | 27 02 539 A1 | 1/1977 |
| DE | 33 36 486 A1 | 4/1984 |
| DE | 86 02 238 U1 | 4/1986 |
| DE | 85 90 143 U1 | 4/1987 |
| EP | 0 028 929 A2 | 5/1981 |
| EP | 0 098 939 A2 | 1/1984 |
| EP | 0 114 617 A2 | 8/1984 |
| EP | 0 063 599 B1 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 949 584 A2 | 10/1999 |
| EP | 1036569 A2 | 9/2000 |
| EP | 1 369 139 A1 | 12/2003 |
| EP | 1 220 802 B1 | 2/2004 |
| FR | 2 743 055 A1 | 7/1997 |
| GB | 998 148 A | 7/1965 |
| GB | 1 058 636 A | 2/1967 |
| GB | 1290484 A | 9/1972 |
| GB | 1 317 315 A | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2267936 A | 12/1993 |
| GB | 2301040 A | 11/1996 |
| GB | 2 348 928 A | 10/2000 |
| GB | 2 414 187 A | 11/2005 |
| JP | 61-55759 U | 4/1986 |
| JP | 62-121670 U | 8/1987 |
| JP | 04-050059 U | 4/1992 |
| JP | 06-26891 A | 4/1994 |
| WO | WO 86/02275 A1 | 4/1986 |
| WO | WO 87/04354 A1 | 8/1987 |
| WO | WO 90/10470 A1 | 9/1990 |
| WO | WO 91/06334 A1 | 5/1991 |
| WO | WO 92/04065 A1 | 3/1992 |
| WO | WO 92/07600 A1 | 5/1992 |
| WO | WO 92/09324 A1 | 6/1992 |
| WO | WO 92/15353 A2 | 9/1992 |
| WO | WO 92/17231 A1 | 10/1992 |
| WO | WO 93/24167 A1 | 12/1993 |
| WO | WO 94/11272 A1 | 5/1994 |
| WO | WO 94/14492 A2 | 7/1994 |
| WO | WO 95/34874 A1 | 12/1995 |
| WO | WO 96/16686 A1 | 6/1996 |
| WO | WO 96/16687 A1 | 6/1996 |
| WO | WO 96/39337 A1 | 12/1996 |
| WO | WO 97/12638 A1 | 4/1997 |
| WO | WO 98/01822 A1 | 1/1998 |
| WO | WO 98/56444 A1 | 12/1998 |
| WO | WO 98/56445 A1 | 12/1998 |
| WO | WO 99/36115 A2 | 7/1999 |
| WO | WO 99/57019 A2 | 11/1999 |
| WO | WO 00/09187 A1 | 2/2000 |
| WO | WO 00/59806 A1 | 10/2000 |
| WO | WO 01/28887 A1 | 4/2001 |
| WO | WO 01/29765 A1 | 4/2001 |
| WO | WO 01/37909 A1 | 5/2001 |
| WO | WO 02/072183 A1 | 9/2002 |
| WO | WO 03/101514 A1 | 12/2003 |
| WO | WO 03/103759 A1 | 12/2003 |
| WO | WO 2004/089451 A1 | 10/2004 |
| WO | WO 2006/110080 A1 | 10/2006 |

OTHER PUBLICATIONS

Translation of Japanese Office Action from Japanese Application No. 2008-019458, dated Sep. 29, 2009, 2 pages.

Office Action from counterpart Japanese Application No. 2008-189362, dated Jun. 14, 2011, 4 pages (with translation).

Extended European Search Report for European Application No. 09173845.0, dated Jun. 25, 2010, 18 pages.

Spirale DDS Product Information sheet, Armstrong Medical, [online] [retrieved from internet: URL http://www.amsorbplus.com/products/spirale/spirale-main.htm], [retrieved on Oct. 21, 2009], 1 page.

Office Action from co-pending U.S. Appl. No. 13/397,284, dated Sep. 6, 2012, 10 pages.

* cited by examiner

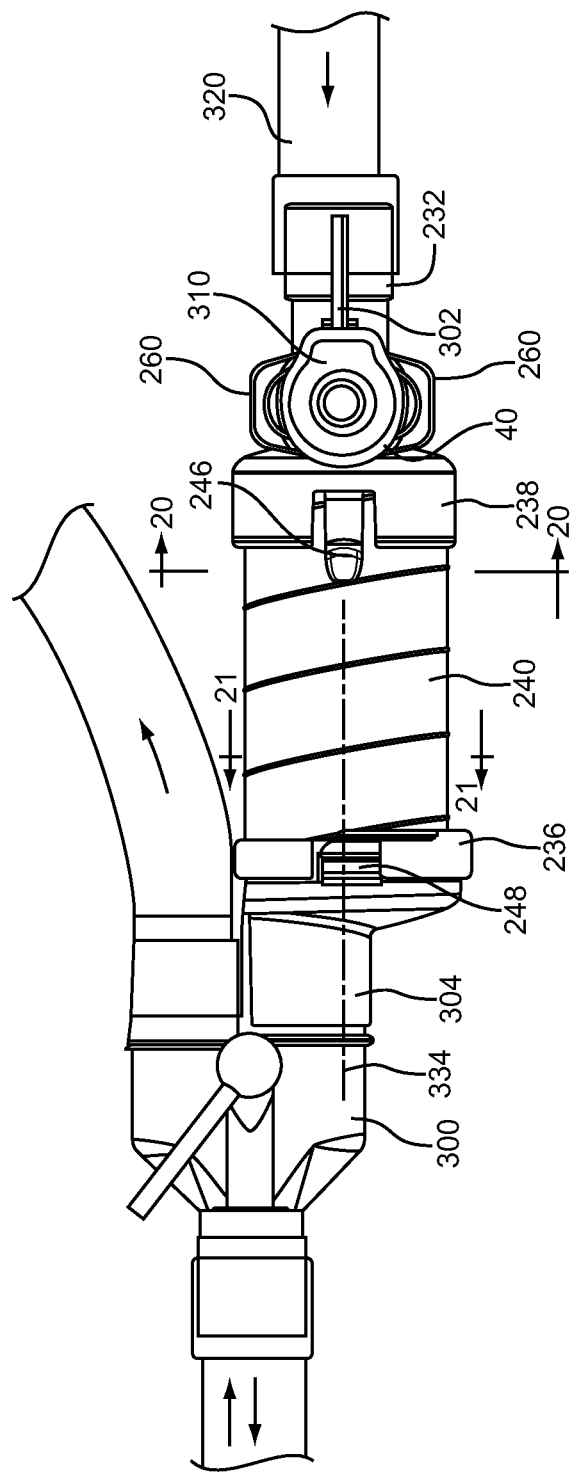

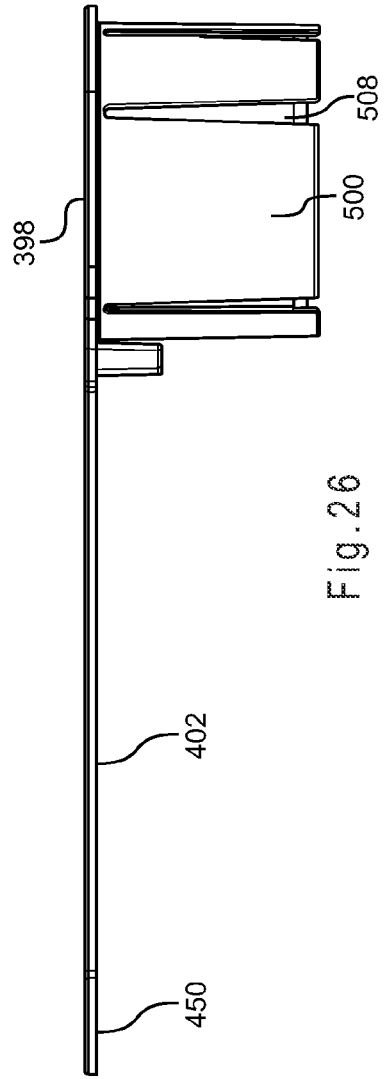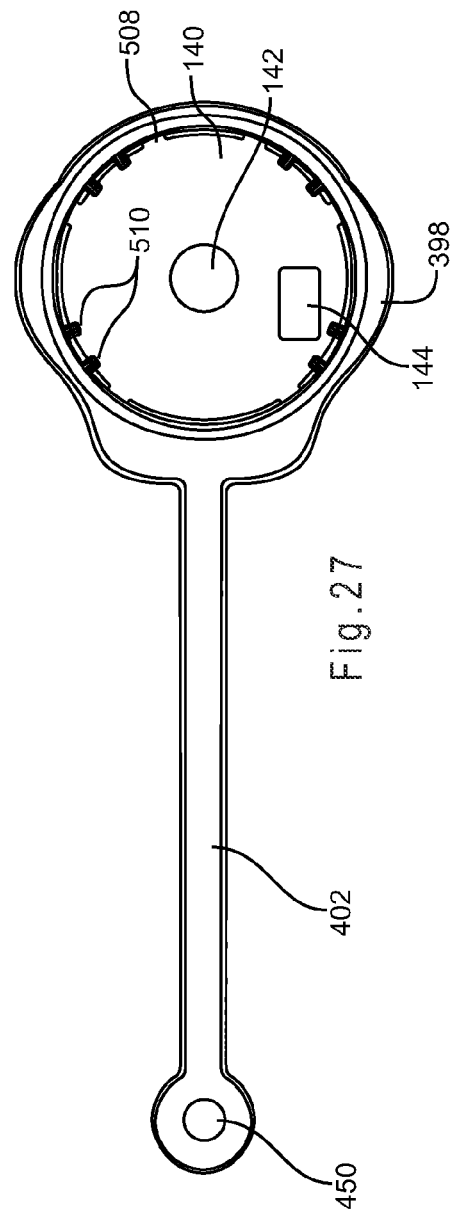

MODULAR AEROSOL DELIVERY SYSTEM

This application claims the benefit of U.S. Provisional Application Ser. No. 61/107,435, filed Oct. 22, 2008, the entire disclosure of which is hereby incorporated herein by reference.

BACKGROUND

The present invention relates generally to an aerosol delivery system, and in particular to a modular aerosol delivery system configured to adapt and support medicament container assemblies having different configurations.

Pressurized Metered Dose Inhalers (PMDI's) are an important delivery mechanism for various medicaments. For example, patients have certain conditions that can be treated with medicaments dispersed in an aerosol and administered to the patient by inhalation. In one format, the aerosol with medicaments is maintained under pressure in a container, and is dispensed in metered, or measured, dosages with an inhalation device, such as an actuator boot. In other arrangements and configurations, the aerosol with medicaments is administered by way of a holding chamber, which can be further incorporated into a ventilator system.

In some circumstances, it can be important for the patient or caregiver to be able to ascertain the number of metered doses remaining in the container, either by an indication of the number remaining therein or by knowledge of the number already dispensed therefrom, such that the patient or caregiver is not caught unaware with an empty container when in need of the medicament. As a result, it is known to secure various indicating devices to the container and/or to the dispenser housing interfacing with the canister. The indicating devices are configured to count and display indicia informing the patient or caregiver about the number of doses used or remaining in the container.

In one example of such a device, as shown for example and without limitation in U.S. Pat. No. 6,431,168, the dose indicator is secured to the container. As such, the corresponding dispenser housing must be shaped to receive a container assembly, which includes the container and dose counter secured thereto. One problem with such a configuration, however, is that the dispenser housing may not be suitably shaped and/or configured to receive and properly actuate a different container assembly, for example a container having a different medication, and which may or may not be equipped with a dose counter or a differently shaped dose counter. This can be particularly troublesome, for example, where the dispenser housing is incorporated into a ventilator circuit and cannot be easily removed therefrom. As such, it may be difficult to administer different types of medication through the same dispenser housing, but instead requires the caregiver to disassemble and reconfigure the ventilator circuit for each type of medication.

For at least these reasons, an improved medication delivery assembly, which can accommodate and actuate different medicament container assemblies, is desirable.

SUMMARY

In a first aspect of the invention, a kit for assembling a medication delivery device includes a dispenser housing having a support block with a well and an orifice communicating with the well. The dispenser housing includes a peripheral wall defining a cavity. A first container assembly includes a valve stem shaped to be received by the well in the support block. The first container assembly has a first exterior shape and is reciprocally moveable along a longitudinal axis defined by the valve stem. The first exterior shape is shaped to be received in the cavity. A second container assembly includes a valve stem shaped to be received by the well in the support block. The second container assembly has a second exterior shape and is reciprocally moveable along a longitudinal axis defined by the valve stem. The second exterior shape is different than the first exterior shape. An insert member is adapted for mounting to the dispenser housing in the cavity and defines an interior space shaped to receive the second exterior shape of the second container. Both the first container assembly and the second container assembly, the latter in combination with the insert member, are adapted to be mounted in the dispenser housing. The first container assembly in combination with the insert member is not adapted to be mounted in the dispenser housing.

In another aspect, a medication delivery device includes a dispenser housing having a support block with a well and an orifice communicating with the well. The dispenser housing includes a first peripheral wall defining a cavity. An insert member is disposed in the cavity of the dispenser housing. The insert member has a second peripheral wall nesting with the first peripheral wall, and a floor defining an interior space. The floor has an opening aligned with the well of the dispenser housing. A medicament container includes a canister and a valve stem, which extends through the opening in the floor and is received in the well in the support block. The canister is reciprocally moveable relative to the valve stem along a longitudinal axis defined by the valve stem.

In yet another aspect, a method for assembling a medication delivery device includes providing first and second identical dispenser housings each having a support block with a well and an orifice communicating with the well. Each of the dispenser housings has a peripheral wall defining a cavity. The method further includes providing a first container assembly having a valve stem shaped to be received by the well in the support block of the first dispenser housing. The first container assembly has a first exterior shape shaped to be received in the cavity of the first dispenser housing, and includes a dose counter. The method further includes inserting the first container assembly in the cavity of the first dispenser housing and disposing the valve stem in the support block of the first dispenser housing. The method also includes providing a second container assembly having a valve stem shaped to be received by the well in the support block of the second dispenser housing. The second container assembly has a second exterior shape different than the first exterior shape. The method further includes disposing an insert member in the cavity of the second dispenser housing. The insert member includes an interior space shaped to receive the second exterior shape of the second container. The method further includes inserting the second container assembly in the interior space of the insert member and disposing the valve stem of the second container assembly in the support block of the second dispenser housing.

In yet another aspect, a ventilator system includes a dispenser housing in fluid communication with an oxygen intake line and a patient interface. The dispenser housing includes a support block having a well and an orifice communicating with the well. The dispenser housing has a peripheral wall defining a cavity. An insert member is adapted for mounting to the dispenser housing in the cavity and defines an interior space. The insert member has a floor with an opening adapted to be aligned with the well of the dispenser housing when the insert member is mounted to the dispenser housing.

In yet another aspect, a method for assembling a medication delivery device includes providing a dispenser housing having a support block with a well and an orifice communicating with the well. The dispenser housing includes a peripheral wall defining a cavity. A first container assembly is inserted in the cavity of the dispenser housing. The method includes removing the first container assembly from the cavity of the dispenser housing, disposing an insert member in the cavity of the dispenser housing, and inserting a second container assembly in the insert member.

In yet another aspect, a medication delivery device includes a first end piece having an input port and a first quick release connector component and a second end piece having an exit port and a second quick release connector component. The first and second quick release connector components are releasably engageable with the first and second end pieces defining an interior space therebetween. A collapsible chamber has opposite ends connected to the first and second end pieces. The collapsible chamber is moveable between a collapsed position and an extended position, wherein an entirety of the collapsible chamber is received in the interior space defined by the first and second pieces when in the collapsed position.

The various aspects and embodiments of the present invention provide significant advantages relative to the prior known devices. In particular, a single dispenser housing can be used to accommodate differently shaped and configured medicament container assemblies. As such, there is no need to manufacture and inventory multiple, complicated and expensive dispenser housings. Instead, a simple and inexpensive insert member can be used to reconfigure the dispenser housing. In addition, this allows the user, such as the caregiver, to use the same dispenser housing to dispense different types of medication, or medications coming in different types of containers. This can be important, for example and without limitation, when the dispenser housing is difficult to remove from a delivery system such as a ventilator system. The collapsible chamber permits the chamber to be collapsed, so as to minimize the size of the device while protecting the chamber from tampering or other damage.

BRIEF DESCRIPTION OF THE DRAWINGS

FIG. 19 is view of a medication delivery device incorporated into a ventilator circuit.
FIG. 26 is a side view of an insert member.
FIG. 27 is a top view of an insert member.

DETAILED DESCRIPTION OF THE DRAWINGS

The present disclosure is directed to medication delivery devices, including ventilator circuit aerosol delivery systems. The disclosed ventilator circuit aerosol delivery systems include implementations to be used with intermittent flow ventilators and implementations to be used with continuous flow ventilators. As described in more detail below, by implementing systems to separate an inspired gas flow from an expired gas flow at the entrance to an endotracheal tube, or a tracheotomy tube, and integrating a Wye connector into an MDI ventilator assembly, the MDI ventilator assembly may be moved from the inspired limb and connected directly to the endotracheal tube, or a tracheotomy tube. By connecting the MDI ventilator assembly directly to the endotracheal tube, or tracheotomy tube, aerosolized drugs may be more effectively administered to a patient without "dead space area" where gases exhaled from a patient remain between each breath such that the same gases are inhaled by the patient upon their next breath. Various delivery systems are disclosed for example and without limitation in U.S. Publication No. US 2005-39746A1, entitled Ventilator Circuit and Method for the User Thereof and filed Feb. 9, 2004, U.S. Publication No. US 2006-0254579A1, entitled Ventilator Circuit and Method for the Use Thereof and filed Apr. 24, 2006, and U.S. application Ser. No. 12/105,881, entitled Aerosol Delivery System and filed Apr. 18, 2008, the entire disclosures of which are hereby incorporated herein by reference.

Figure 1:
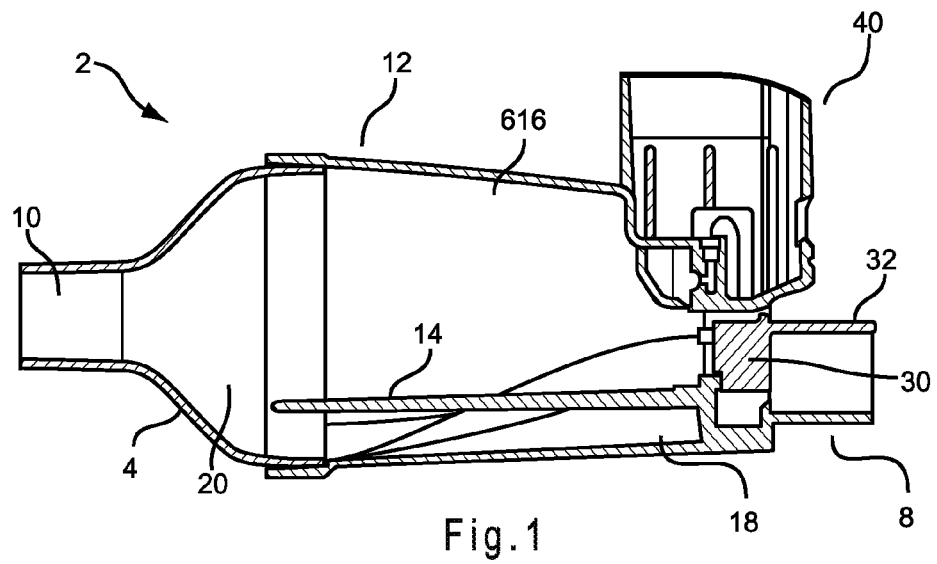
FIG. 1 is a cross-sectional, side view of a first embodiment of a dispenser housing including a holding chamber.
Figure 15:
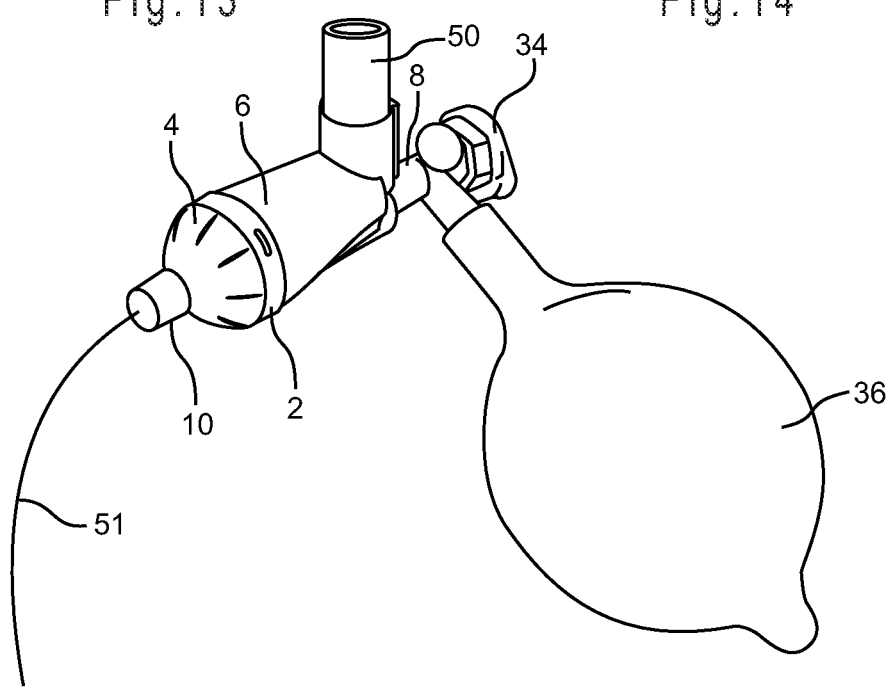
FIG. 15 is a perspective view of a medication delivery device including a resuscitation bag.
Figure 16:
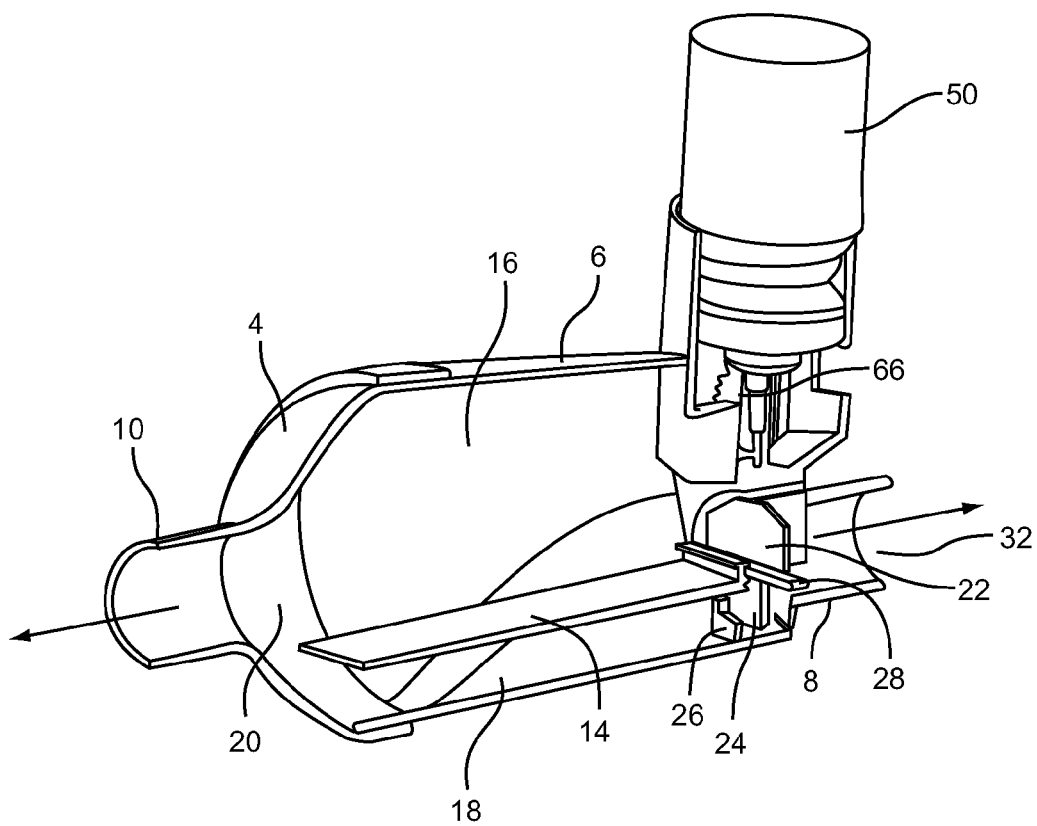
FIG. 16 is a partial, perspective view of a medication delivery device shown in FIG. 15.

Now referring to the embodiment of FIGS. 1, 15 and 16, a dispenser housing 2 includes three primary components. A housing component 4 includes a patient port 10. It should be understood that the housing component 4 can be configured with different patient ports to accommodate various patient interface components, including for example and without limitation endotracheal (ET) tubes, masks, mouthpieces, etc. A second housing component 6 includes an exterior wall 12 and an interior wall 14, or shelf, which separates the chamber into the inhalation and exhalation interior spaces 16, 18. In one embodiment, the spaces 16, 18 communicate with each other at a vestibule area 20 formed in front of and communicating with the patient port. A receptacle 40 is formed on the housing and includes a support block 42 having a well 44 with an orifice 46 that communicates directly with the inhalation interior space 16, as shown in FIGS. 3-10.

Referring again to FIGS. 1, 15 and 16, a third housing component 8 is formed as a connector and defines a ventilator port 32. The connector has first and second passageways separated by a wall, with the first and second passageways communicating with inhalation and exhalation interior spaces 16, 18. Additional walls 30 form a valve seat for the inhalation valve 22. The first and third components 4, 8 are secured to respective ends of the second component 6 to form the dispenser housing. An integrally formed inhalation/exhalation valve 22, 24 is disposed between the connector 8 and the second component 6. The second component 6 has a valve seat 26 for the exhalation valve 24. The valve includes a base portion 28, and inhalation/exhalation flaps 22, 24 extending in opposite directions from the base portion 28. The inhalation valve 22 moves off of the first seat 30 of the connector 8 during inhalation, while the exhalation valve 24 moves off of the second seat 26 during exhalation. In one embodiment, the surface area of the inhalation valve 22 is greater than the surface area of the exhalation valve 24, although it should be understood that the surface areas can be the same, or that the surface area of the inhalation valve is less than the area of the exhalation valve. It should be understood that the inhalation and exhalation valves 22, 24 can be formed separately, again with the same or differential surface areas.

In operation, the system is pressurized to inflate the lungs of the patient, such as a neonate. The positive pressure comes from an oxygen supply 34 connected to a resuscitation bag 36. Manual resuscitation, for example and without limitation bagging, can begin immediately after birth, for example, to maintain a neonate's breathing. A pressurized metered dose inhaler (pMDI) 50 is actuated or fired in between breaths, with the drug being held in the inhalation interior space 16 of the chamber until the next breath. As the resuscitation bag is squeezed, the flow through the inhalation valve 22 and increase in pressure forces the drug from the inhalation interior space 16 of the chamber through the patient port 10 to the patient, for example through the endotracheal tube 51. As the resuscitation bag 36 reinflates, it creates a negative pressure that pulls air through the exhalation interior space 18 as the exhalation valve 24 is opened, with any drug remaining in the inhalation interior space 16 staying there due to the separation of the inhalation and exhalation interior spaces 16, 18. The next breath forces the remaining drug through the patient port 10 to the patient through the patient interface component. The dispenser housing can be used with a flow inflating resuscitation bag, as described hereinabove, or with a self-inflating resuscitation bag. The self-inflating resuscitation bag includes a non-rebreathing valve that prevents the bag from pulling exhaled gases from the patient, and in particular from the chamber. Instead, the patient exhales into the device and the expiratory gases exit to the atmosphere through the non-breathing valve. With this device, the dispenser housing still separates the exhaled gases because a pressure differential is maintained with a higher pressure at the patient end of the device.

While the embodiments of FIGS. 1, 15 and 16 may still be used with a Wye connector, it should be understood that because inspired gas flow and expired gas flow are separated at the entrance to the endotracheal breathing tube, or tracheotomy tube, the MDI ventilator assembly may be moved from the inspired limb and connected directly to the endotracheal breathing tube or tracheotomy tube.

Figure 21:
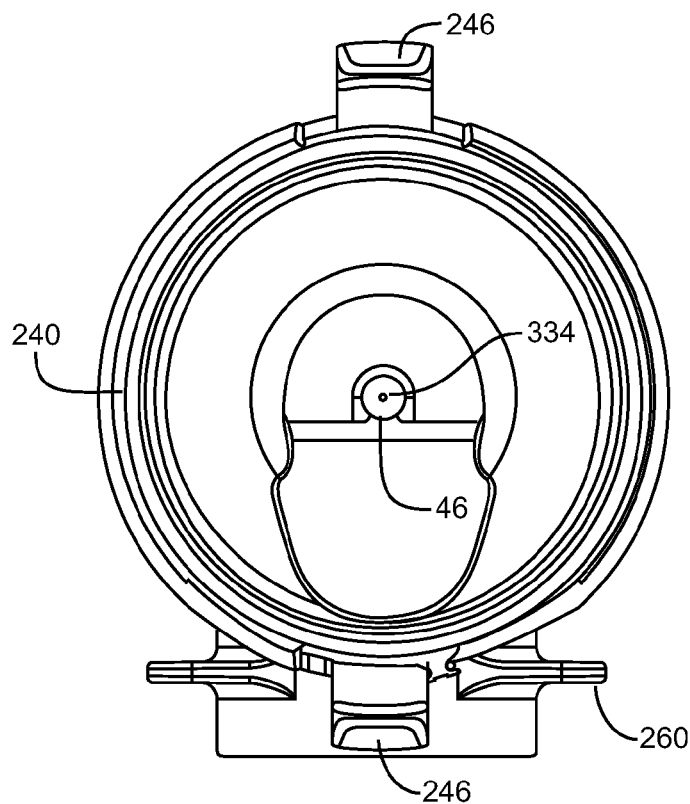
FIG. 21 is a cross-sectional view of the delivery device shown in FIG. 19 taken along line 21-21.
Figure 20:
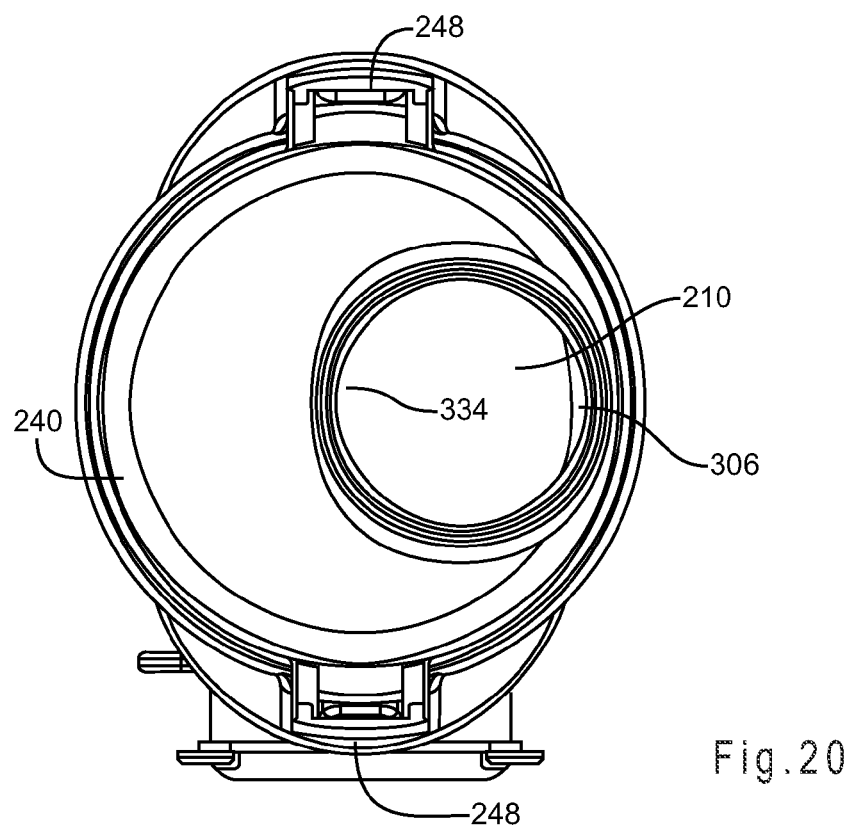
FIG. 20 is a cross-sectional view of the delivery device shown in FIG. 19 taken along line 20-20.
Figure 22:
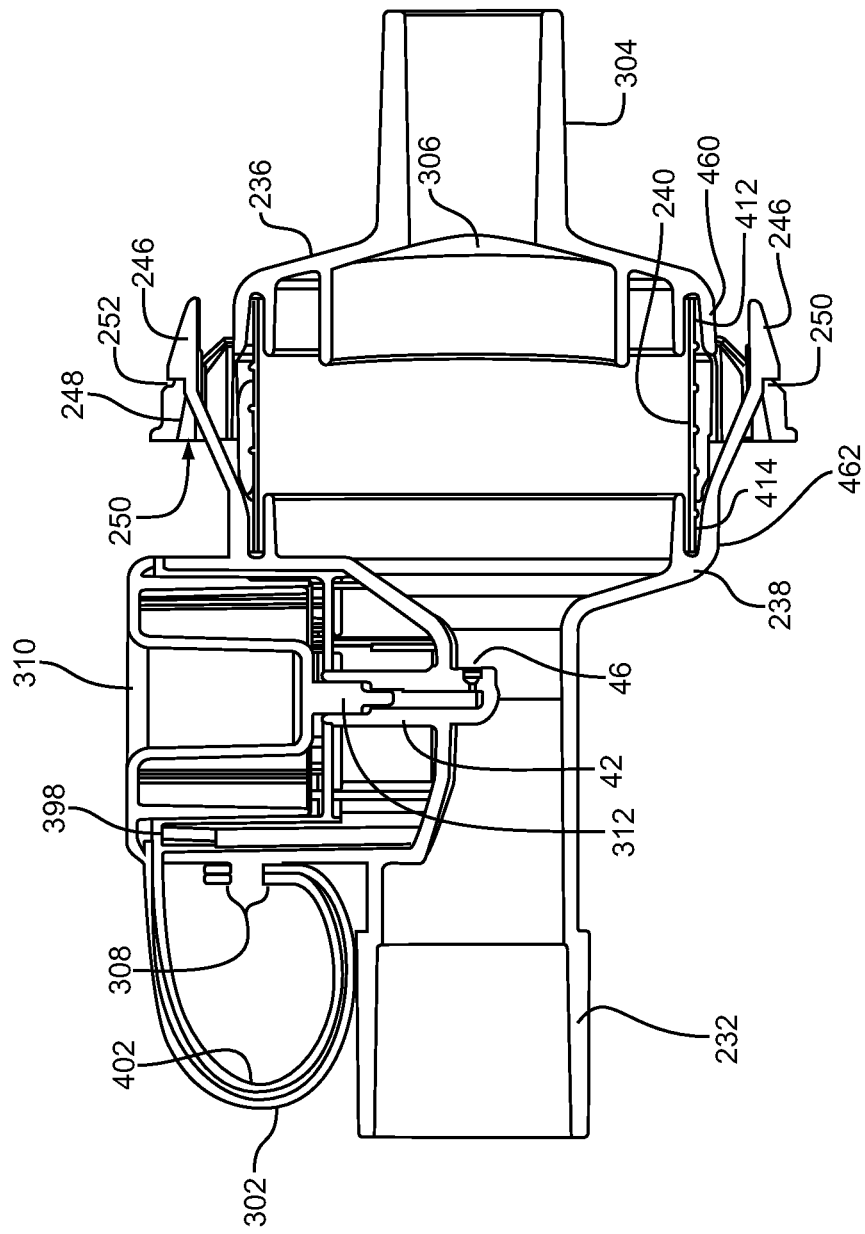
FIG. 22 is a side cross-sectional view of a delivery device shown in a collapsed position.
Figure 23:
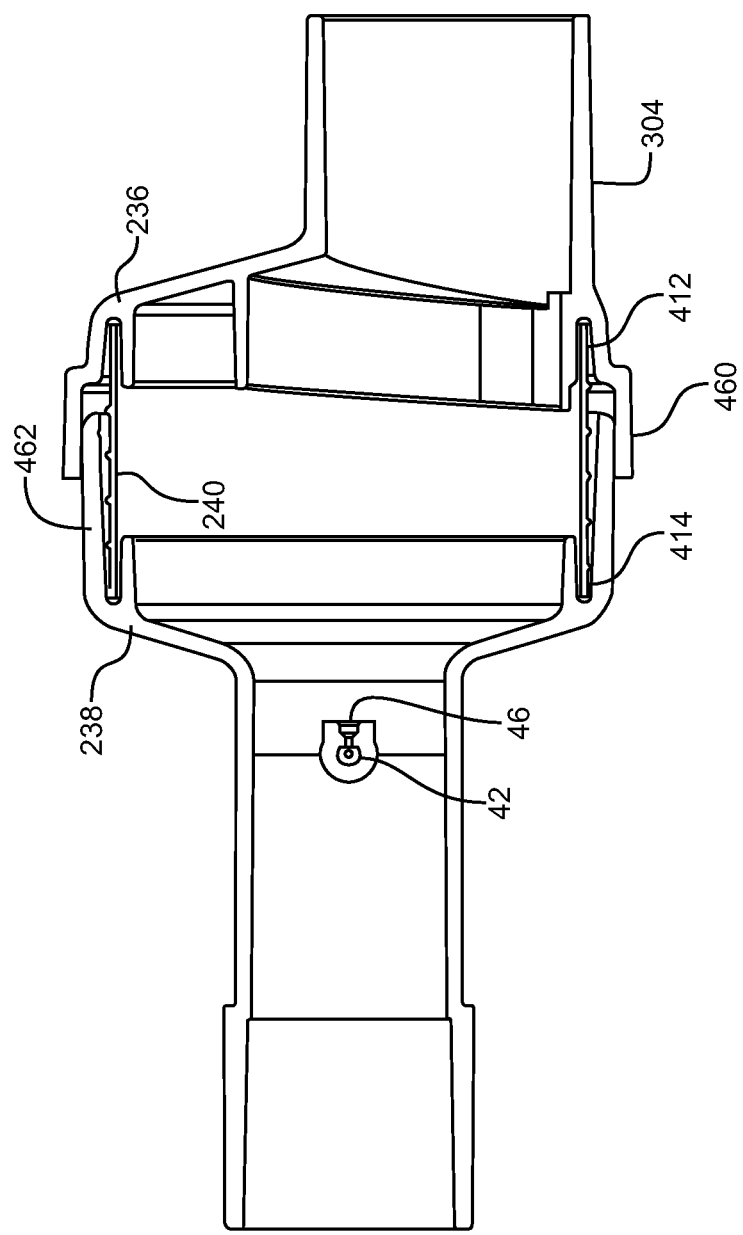
FIG. 23 is a top cross-sectional view of a delivery device shown in a collapsed position.
Figure 24:
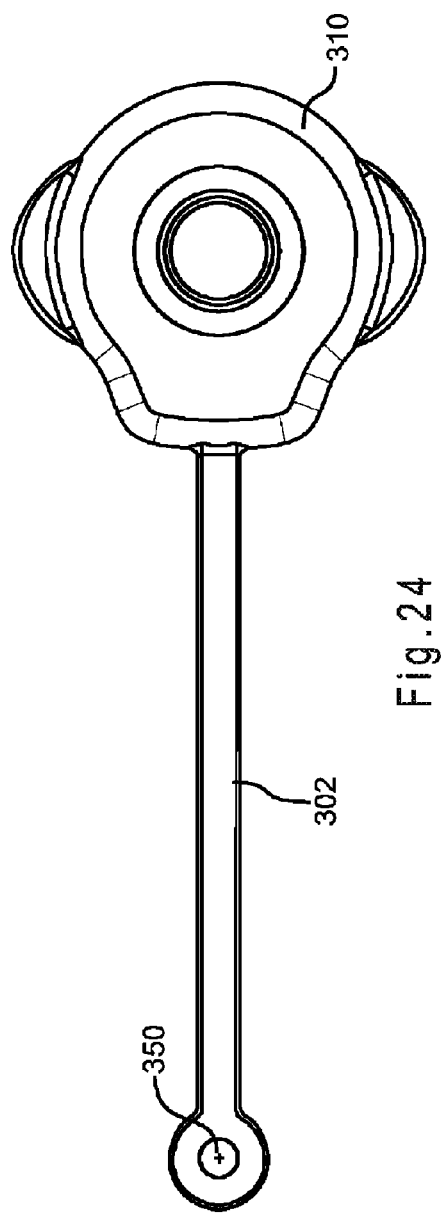
FIG. 24 is a plan view of a plug member.
Figure 25:
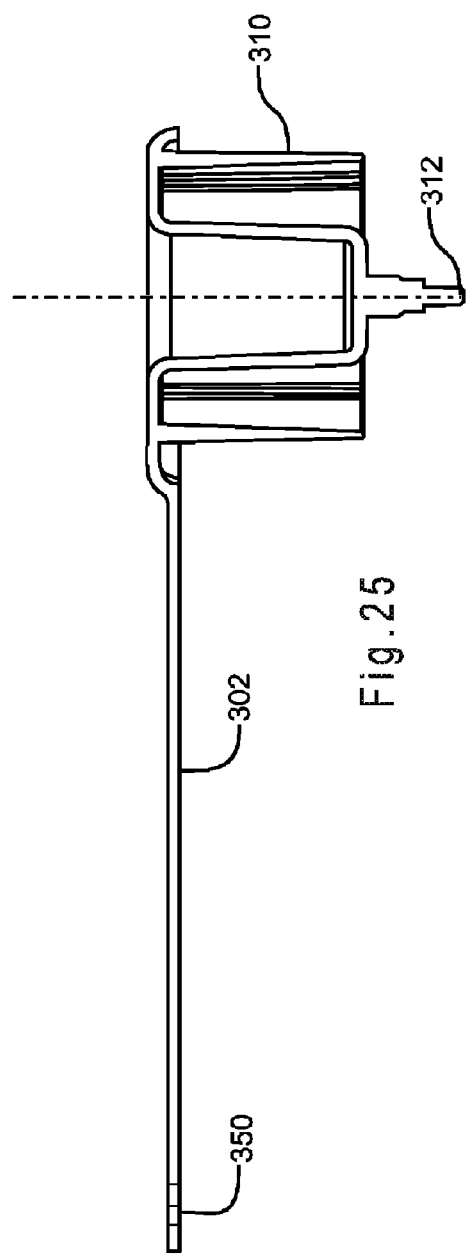
FIG. 25 is a side, cross-sectional view of the plug member shown in FIG. 24.

The disclosed ventilator circuit aerosol delivery system is suitable for use with intermittent flow ventilators and continuous flow ventilators, and including without limitation both mechanical and manual ventilators such as resuscitation bags. As used herein throughout, the term "including" does not means limited to, but rather is without limitation. Implementations of the disclosed ventilator circuit aerosol delivery systems provide the ability to connect the MDI ventilator assembly directly to the endotracheal tube, or a tracheotomy tube, due to an integrated Wye connector or the ability to separate inhalation flow and exhalation flow at the entrance to an endotracheal breathing tube or a tracheotomy tube. Connecting the MDI ventilator assemblies directly to the endotracheal tube, or tracheotomy tube, provides the ability to more efficiently administer aerosolized drugs to a patient without "dead space area" where gases exhaled from a patient remain between each breath such that the same gases are inhaled by the patient upon their next breath. For this reason, the MDI ventilator assembly may be left in a ventilator circuit even when the MDI ventilator assembly is not being used to administer an aerosolized drug to a patient so that it is no longer necessary to break a ventilator circuit each time an aerosolized drug is administered to a patient.

Preferably, the housing 2, or it various components 4, 6, 8 individually or in combination, are made of a clear plastic, although it can be non-transparent in certain embodiments. In one implementation, the housing 2, or its various components individually or in combination, may be made from an anti-static material such that a surface resistivity of the housing 2 is less than about 10E12 ohm/sq., and preferably between about 10E10 and about 10E12 ohm/sq. Examples of antistatic housings are disclosed in U.S. patent application Ser. No. 10/821,260, filed Apr. 8, 2004, the entirety of which is hereby incorporated by reference. Further examples of housings used in MDI ventilator assemblies are disclosed in U.S. patent application Ser. No. 10/774,751, filed Feb. 9, 2004 and published as U.S. Publication No. US 2005-39746A1 (entitled Ventilator Circuit and Method for the User Thereof), and U.S. patent application Ser. No. 11/410,270, filed Apr. 24, 2006 U.S. and published as U.S. Publication No. US 2006-0254479A1 (entitled Ventilator Circuit and Method for the User Thereof), the entire disclosures of which are hereby incorporated herein by reference.

It should be appreciated that the housing 2 may additionally define a temperature probe port, a pressure port, and a holder. In one implementation, both the temperature probe port and the pressure port are positioned on the inhalation port. However, in other implementations, one or both of the temperature probe port and the pressure port may be positioned on other portions of the housing such as the exhalation port. It should be understood that the ports, including without limitation the temperature and pressure ports, can be used to monitor other parameters, such as the presence of $CO_2$ or other gases.

Referring to FIGS. 17-23, another embodiment of a medication delivery device includes a housing 202 having a port 232 and a patient port 210, 304. The port 232 can be configured as a ventilator port as described above with respect to the first embodiment. Indeed, as shown in the embodiment of FIG. 19, a WYE-connector 300 is connected to the patient port 304, with a ventilator supply conduit 320 connected to the port 232. As shown in FIGS. 19, 21 and 23, in one embodiment, the patient port 304 is offset from a central, longitudinal axis 334 defined by the chamber, while the orifice 46 is in line with the longitudinal axis 334. A receptacle 40 is configured on a conduit 234 communicating between the port and the housing. The housing includes first and second end pieces 236, 238, with the first end piece including the patient port 210, 304. As shown in FIGS. 21-23, the patient port 304 includes a curved portion 306. A collapsible chamber 240 is disposed between and coupled to the end pieces. U.S. Pat. No. 4,938,210, which is hereby incorporated herein by reference, discloses one embodiment of a collapsible chamber. The chamber defines an interior space. When extended, the chamber has a volume of less than about 150 cc in one embodiment, less than about 130 cc in another embodiment, and less than about 125 cc in another embodiment. The chamber is expandable between a collapsed, stored position (FIGS. 22 and 23) and an extended, use position (FIGS. 17-21). In the stored position, the chamber is collapsed and disposed in spaces 242, and in particular annular grooves 412, 414, formed by the end pieces, which are coupled for example with a quick-release mechanism 244 that can be snapped together. In the stored position, the collapsible chamber is protected from tampering, with the size of the overall device being reduced. In one embodiment, the quick release mechanism includes first and second connector components, which may be interchanged on the first and second end pieces. In one embodiment, the quick release mechanism includes a pair of tabs 246 releasably engaging a corresponding pair of receivers 248 configured with abutment surfaces 252. The tabs are depressed, inserted through openings 250 in the receivers and then released to engage the surfaces. The tabs include grippable portions 254 allowing them to be engaged by the user and thereafter deflected for engagement/insertion and disengagement/withdrawal with the receivers. In the collapsed position, an entirety of the collapsible chamber is received in the interior space 242, 412, 414 defined by the first and second pieces. In one embodiment, each of the first and second end pieces include an annular wall 460, 462 defining the interior space 242, 412, 414, with the annular walls 460, 462 overlapping when the collapsible chamber is moved to the collapsed position as shown in FIGS. 22 and 23. The discharge orifice 46 is in fluid communication with the interior of the collapsible chamber.

Figure 17:
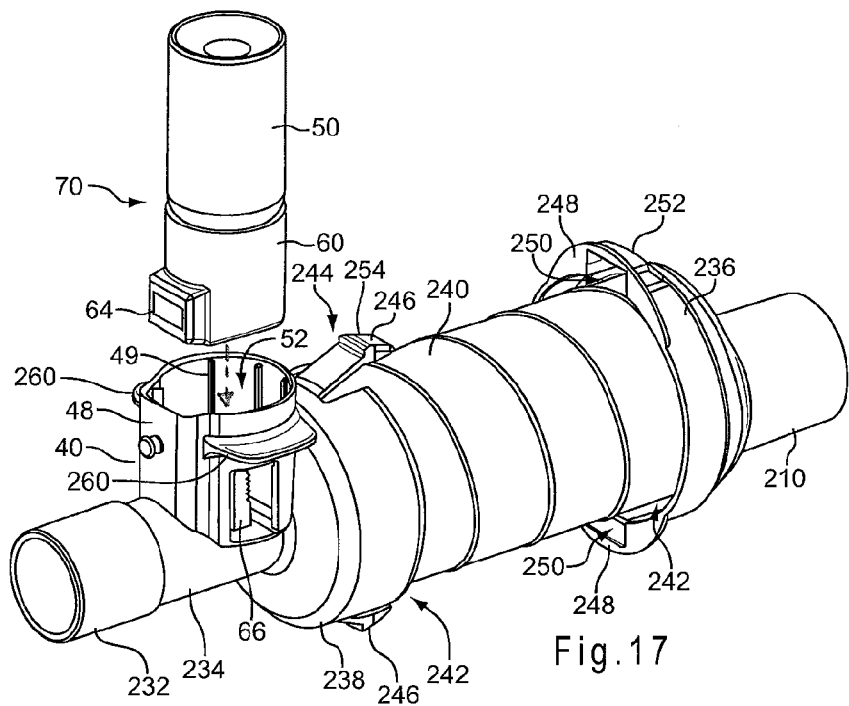
FIG. 17 is a partially exploded perspective view of an alternative embodiment of a medication delivery device.
Figure 18:
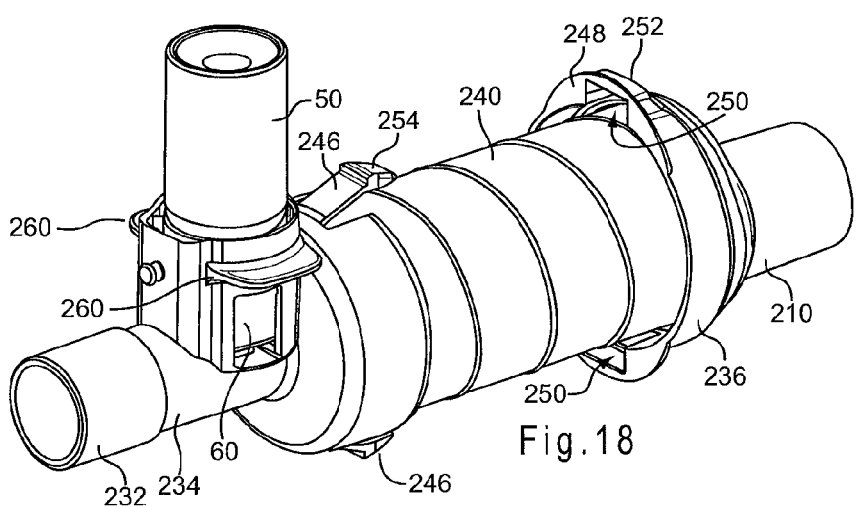
FIG. 18 is an assembled perspective view of the medication delivery device shown in FIG. 17.

Referring to FIGS. 1, 3-6, 10, 15 and 16, the MDI receptacle 40 is typically located on a top of the housing 2, but the MDI receptacle 40 may be located at other positions on the housing 2, for example on the conduit as shown in FIGS. 17 and 18. FIGS. 3-6 and 10-14 presently show only the downstream portion of the housing component 6, and it should be understood that this portion can be made separately or integrally with the remaining portions of housing component 6, or components 4 and 8. The MDI receptacle 40 is positioned away from the patient port 10 such that when an aerosolized drug is dispensed into the interior space 16 via the MDI receptacle 40, the aerosolized drug may expand before being inhaled by a patient via the patient port 10. In particular, it will be appreciated that during inhalation, when gases flow from the interior space 16 to the endotracheal breathing tube, or tracheotomy tube, the aerosolized drug expands and flows to the patient. If any portion of the aerosolized drug is not inhaled during an initial breath, the remaining aerosolized drug is inhaled during subsequent breaths.

Referring to FIGS. 3-6, 10-14 and 17, the MDI receptacle 40 includes a peripheral wall 48 that defines a socket or recess 52 to receive an end of a MDI container 122 such that when the MDI container 50 is placed in the MDI receptacle 40, an actuator nozzle 42 or support block in the recess of the MDI receptacle 40 engages a stem 54 extending from the MDI container 50 and causes the aerosolized drug within the MDI container 50 to be dispensed into the interior space 16 of the housing 2. A plurality of longitudinal ribs 49 are formed along the interior surface of the wall 48. In particular, the stem 52 is received in the well 44 formed in the actuator nozzle or support block 42. The well 44 communicates with the discharge orifice 46, which opens into the interior space 16. It should be understood that the receptacle can be configured to connect to and support medication containers, aerosol dispersal devices, or systems other than the disclosed MDI container 50.

Figure 2:
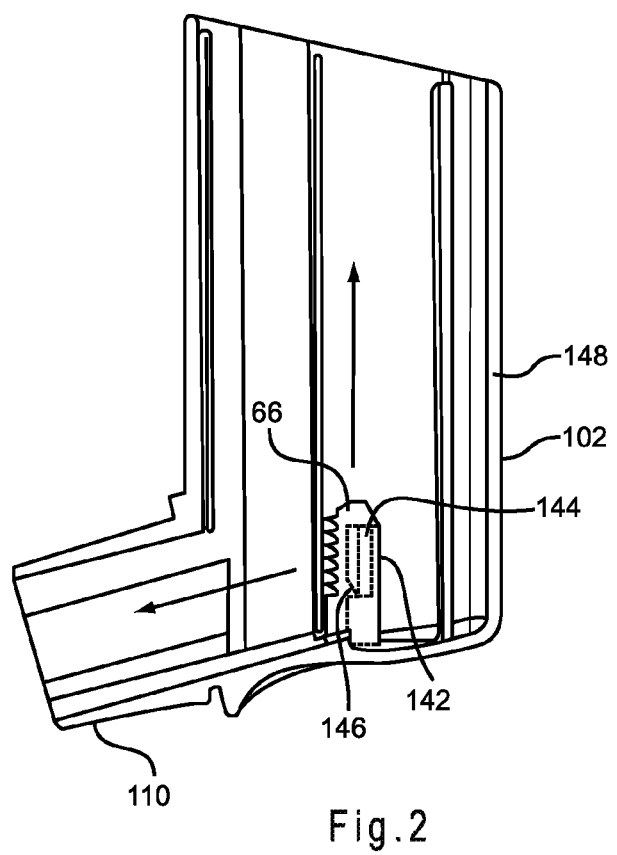
FIG. 2 is a cross-sectional, side view of a second embodiment of a dispenser housing.
Figure 3:
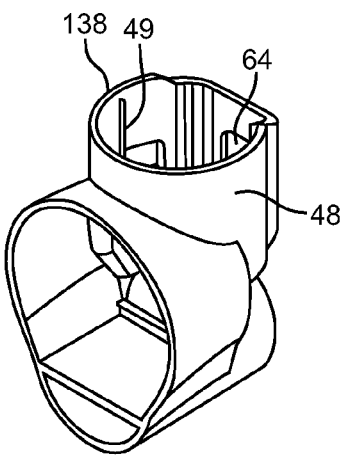
FIG. 3 is a perspective view of a portion of the dispenser housing shown in FIG. 1.
Figure 4:
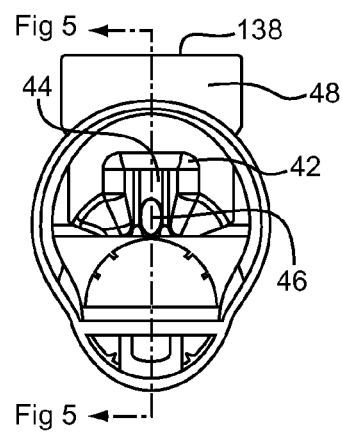
FIG. 4 is a front view of the dispenser housing portion shown in
FIG. 3.
Figure 5:
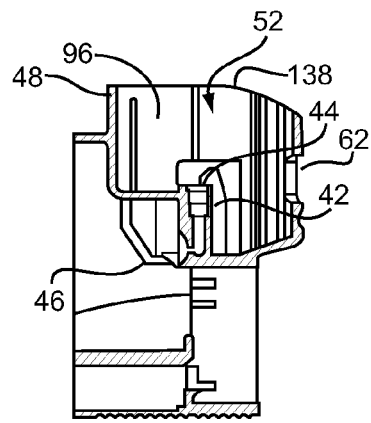
FIG. 5 is a cross-sectional side view of the dispenser housing portion taken along line 5-5 of FIG. 4.

In an alternative embodiment, shown in FIG. 2, a dispenser housing 102 is formed as an actuator boot, with a mouthpiece 110 and a peripheral wall 148 defining a cavity 152 or interior space. Again, the housing includes a support block 142 configured with a well 144 and discharge orifice 146.

Referring to the embodiment of FIGS. 17 and 18, the receptacle is configured with two laterally extending tabs or wings 260. In this embodiment, the user positions two fingers (e.g., first and second) underneath the wings 260 and actuates the container with a thumb. As such, the fingers and thumb do not have to span as great a distance as the other embodiments, for example engaging the bottom of the housing component 8 opposite the container. The wings may also be incorporated into the other embodiments, including for example and without limitation the embodiment of FIGS. 1 and 2. The wings are sized and shaped to provide sufficient surface area to grip. For example and without limitation, in one embodiment, the wings have a depth of about 6 mm and a width of about 18 mm.

Figure 6:
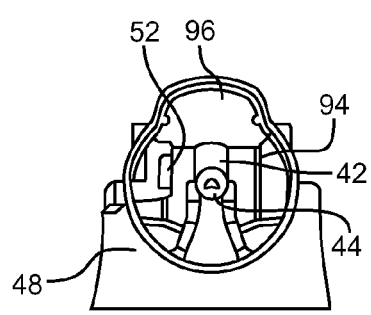
FIG. 6 is a top view of the dispenser housing portion shown in FIG. 3.
Figure 7:
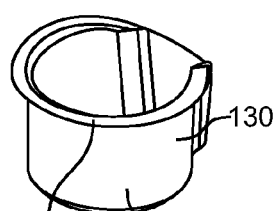
FIG. 7 is a perspective view of an insert member shaped to be received in the dispenser housing shown in FIG. 1.
Figure 8:
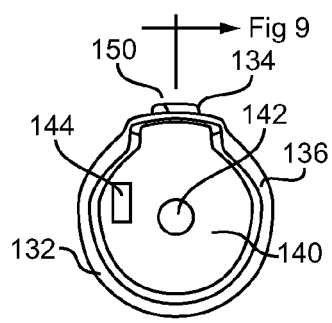
FIG. 8 is a top view of the insert member shown in FIG. 7.
Figure 11:
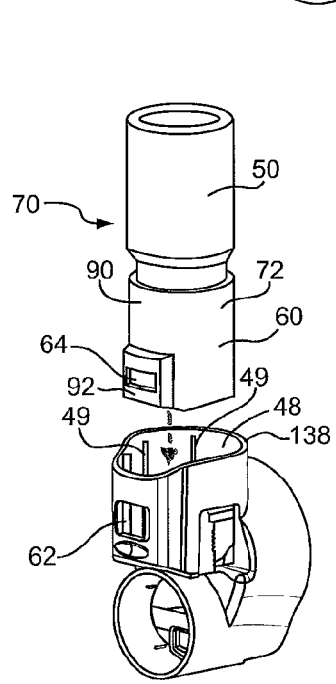
FIG. 11 is an exploded perspective view of a first container assembly and dispenser housing.
Figure 13:
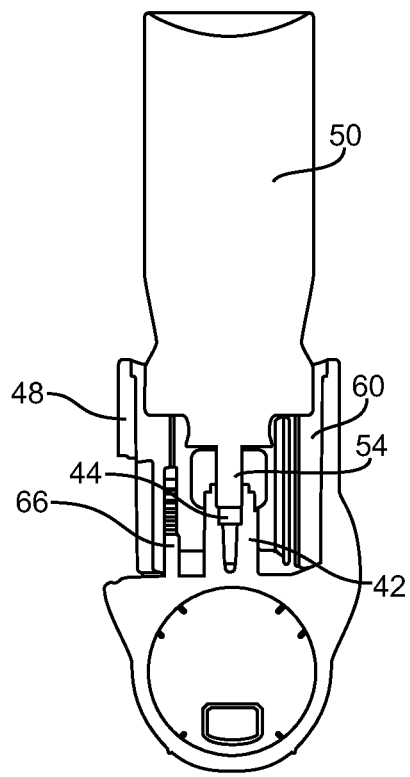
FIG. 13 is a cross-sectional view of the first container assembly and dispenser housing in an assembled configuration.

Referring to FIGS. 11, 13 and 17, a first container assembly 70 includes a dose counter 60 secured to a container 50. The dose counter 60 includes a counting mechanism, mechanical or electrical, including for example and without limitation mechanisms disclosed in U.S. Pat. Nos. 6,997,349 and 6,729,330 (the entire disclosures of which are hereby incorporated herein by reference), with a viewing window 64 displaying various dosage indicia, whether mechanical or electrical/digital. The peripheral wall 48 of the dispenser housing is also configured with a viewing window 62 or opening shaped and positioned to be aligned with the viewing window 64 of the dose counter when the valve stem 54 of the first container assembly is secured in the well 44 of the dispenser housing. Alternatively, the viewing window may be omitted from the dispenser housing as shown in FIGS. 17 and 18, although it should be understood that a viewing window may be incorporated into the embodiment of FIGS. 17 and 18. As shown in FIGS. 2, 13 and 17, an upright member 66 or finger is configured as an actuator. The actuator is positioned such that reciprocal movement of the first container assembly relative to the dispenser housing causes the dose counter to advance and record a dispersement of medication. The first container assembly 70, including the dose counter 60, has a first exterior shape 72 defined by the exterior surface of the dose counter 60, including the viewing window 64. For example, in a cross-section substantially perpendicular to a longitudinal axis defined by the valve stem 54, the cross section substantially mates with the interior space of the socket 52 as shown in FIG. 6, and includes a circular portion 90 and a protuberance 92 extending outwardly from a diameter of the circular portion, thereby forming a "keyhole" shape. The circular portion 90 and protuberance 92 mate with a circular portion 94 of the socket and a recess 96 extending laterally outwardly therefrom respectively.

Figure 12:
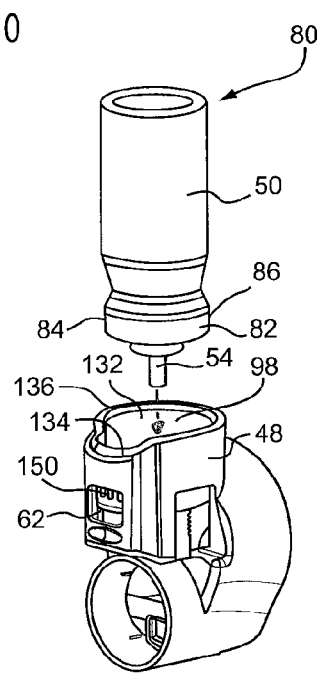
FIG. 12 is an exploded perspective view of a second container assembly and a dispenser housing configured with an insert member.
Figure 14:
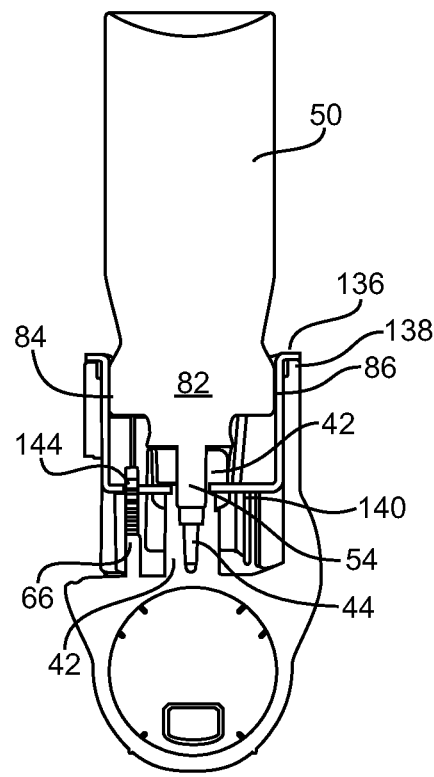
FIG. 14 is a cross-sectional view of the second container assembly and dispenser housing in an assembled configuration.

Referring to FIGS. 12 and 14, a second container assembly 80 is configured as a canister 50 with an end portion 82, including a ferrule, and a valve stem 54 extending therefrom. The second container assembly 80 has a second exterior shape 84 defined by the exterior surface 86 of the end portion of the canister. For example, as shown in FIG. 12, the second exterior shape 84 in cross section is substantially circular defined by the diameter of the end portion. As shown in FIGS. 11 and 12, the second exterior shape 84 of the second container assembly is different than the first exterior shape 72 of the first container assembly. It should be understood that other container assemblies may have further additional, different exterior shapes defined for example and without limitation by differently sized and shaped canisters, e.g., with end portions having different diameters, with or without differently configured and shaped dose counters.

Since the second exterior shape 84 of the second container assembly is different than the first exterior shape 72 of the first container assembly, and in particular has a smaller overall cross-sectional area taken perpendicular to the longitudinal axis defined by the valve stem 54, the second container assembly 80 may feel sloppy relative to the socket 52 when mounted to the support block 42 due to the excess room between the exterior surface of the canister 50, and the end portion in particular, and the interior surface of the peripheral wall 48 of the dispenser housing.

To improve the fit of the second container assembly 84, an insert member 98, 398 is provided, as show in FIGS. 6-10, 12, 14, 22, 26 and 27. The insert member has a peripheral wall 100, 500 that is nested inside the peripheral wall of the dispenser housing and has an exterior shape 130 that mates with the interior profile of the dispenser housing wall. As shown in FIGS. 26 and 27, the wall 500 may include slots 508, as well as ribs 510 that engage the container. In one embodiment, the exterior shape includes a circular portion 132 and a protuberance 134. The insert member further includes an upper peripheral rim 136, 502 that extends outwardly from the peripheral wall and engages a top edge 138 of the dispenser housing wall. The insert member 98, 398 is configured with a floor 140 having an opening 142 aligned with and positioned above the support block and well and shaped to receive the valve stem 54 of the canister. Alternatively, the support block can extend through the floor, as long as the discharge orifice is located beneath the floor and in communication with the holding chamber or mouthpiece. The floor 140 also includes a second opening 144 shaped to receive or accommodate the upright finger 66 or actuator, which may not have any function relative to a second container assembly not configured with a dose counter. The insert member 98, 398 supports the canister 50 during insertion and use, and prevents the valve stem 54 from missing the well 44 during insertion. The floor 140, with its opening 142, further helps locate and align the valve stem 54 with the support block 42 and well 44. In connection with the embodiment of FIG. 2, the insert member may be longer with an upper rim engaging the top of the actuator, or the insert member may not be configured with a peripheral rim.

As shown in FIGS. 19, 22, 26 and 27, the insert member 398 includes a flexible tether 402 having an end portion 450 with an opening that is secured over a button 308 extending from the exterior surface of the receptacle 40. It should be understood that the tether can be integrally formed with the insert member, or can be configured as a separate member, whether formed as a cord, chain, retractable member, or other similar device. In this way, the insert member 398 can be removed, for example when a first container assembly 70 with a dose counter 60 is being used with the dispenser system, but with it remaining connected to the dispenser system with the tether 402 such that it is not lost or otherwise displaced. As shown in FIGS. 19, 22, 24 and 25, a plug member 310, having wings 332 for gripping by the user, can be inserted into the insert member 398 when the system is not in use, or when the insert member is disconnected from the receptacle, so as to prevent contaminants from entering the insert member or receptacle. The plug member 310 includes a tether 302 having an end portion with an opening, which can be secured over the button. It should be understood that the tether can be integrally formed with the insert member, or can be configured as a separate member, whether formed as a cord, chain, retractable member, or other similar device. The plug member 310 includes an orifice insert 312 that is disposed in the well of the support block to plug the well and prevent contamination thereof. The insert 312 extends through the opening 142 in the bottom of the insert member 398.

Figure 9:
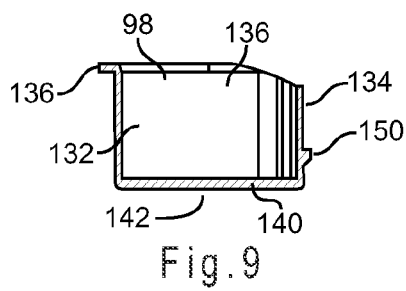
FIG. 9 is a cross-sectional side view of the insert member taken along line 9-9 of FIG. 8.
Figure 10:
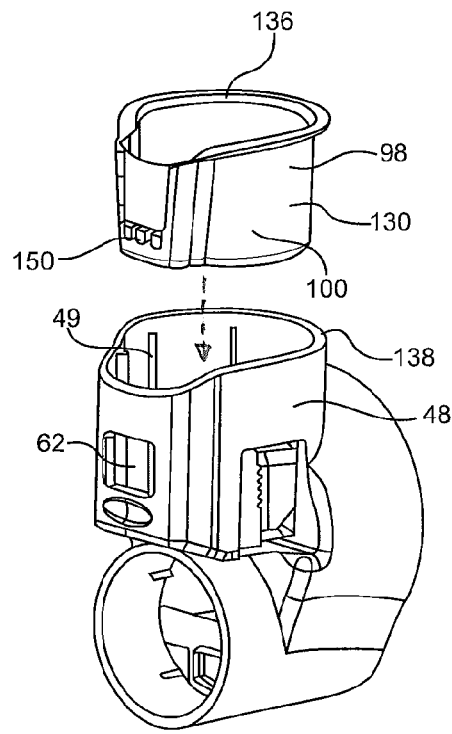
FIG. 10 is an exploded perspective view of an insert member and a portion of a dispenser housing.

In operation, the user, such as caregiver, can use different container assemblies 70, 80, having different exterior shapes 72, 84, with the same dispenser housing 2, 102. For example and without limitation, the caregiver can first dispose the first container assembly 70 with dose counter 60 in the dispenser housing 2, 102, and in particular the socket 52, and actuate the first container assembly a predetermined number of times, including for example a single actuation. The dose counter 60 records the predetermined number of actuations. The caregiver can then remove the first container assembly 70 without having to remove the dispenser housing 2, for example, from a ventilator circuit, or alternatively without having locate another actuator 102 for use with another container assembly. Subsequently, for example if a different medication is required, the caregiver can install an insert member 98, 398 into the dispenser housing 2, 102 and then insert a second container assembly 80, for example a canister 50 without a dose counter, into the insert member 98, 398 and engage the support block 42 of the dispenser housing with the valve stem 54 of the canister. The insert member 98 can be installed in the dispenser housing with a snap-fit, a press fit or any other suitable mechanism for securing the insert member. For example, as shown in FIG. 9, one embodiment of the insert member 98 includes a tab 150 that engages the upper edge of the viewing window 62 with a snap fit as shown in FIG. 12. This same operation can be carried out with the actuator boot shown in FIG. 2, with the insert member configured as needed to be fitted in the boot (e.g., without a rim). In this way, it should be understood that the system and method may be incorporated into systems other than ventilator circuits, including the actuator boot of FIG. 2 and/or a spacer configuration.

It is intended that the foregoing detailed description be regarded as illustrative rather than limiting, and that it be understood that it is the following claims, including all equivalents, that are intended to define the spirit and scope of this invention.

The invention claimed is:

1. A kit for assembling a medication delivery device comprising:
    a dispenser housing comprising a support block having a well and an orifice communicating with said well, said dispenser housing comprising a peripheral wall defining a cavity at least partially surrounding said support block;
    a first container assembly comprising a valve stem shaped to be received by said well in said support block, said first container assembly having a first exterior shape and being reciprocally moveable along a longitudinal axis defined by said valve stem, wherein said first exterior shape is defined in a cross section perpendicular to said longitudinal axis, wherein said first exterior shape is shaped to be received in said cavity;
    a second container assembly comprising a valve stem shaped to be received by said well in said support block, said second container assembly having a second exterior shape and being reciprocally moveable along a longitudinal axis defined by said valve stem, wherein said second exterior shape is defined in a cross section perpendicular to said longitudinal axis, wherein said second exterior shape is different than said first exterior shape; and an insert member adapted for mounting to said dispenser housing in said cavity and defining an interior space shaped to receive said second exterior shape of said second container;

wherein both of said first container assembly and said second container assembly in combination with said insert member are adapted to be mounted in said dispenser housing, wherein said valve stem of said first container is received in said well in said support block when said first container assembly is mounted in said dispenser housing, and wherein said valve stem of said second container is received in said well in said support block when said second container assembly in combination with said insert member is mounted in said dispenser housing, and wherein said first container assembly in combination with said insert member is not adapted to be mounted in said dispenser housing.

2. The kit of claim 1 wherein said insert member has a third exterior shape shaped to be received in said cavity.

3. The kit of claim 1 wherein said insert member comprises a floor having an opening therethrough, wherein said opening is aligned with said well when said insert member is mounted in said dispenser housing.

4. The kit of claim 1 wherein said first container assembly comprises a container filled with a medicament and a dose counter secured to said container.

5. The kit of claim 4 wherein said dispenser housing comprises an actuator member adapted to interface with said dose counter.

6. The kit of claim 5 wherein said actuator member comprises an upright finger.

7. The kit of claim 5 wherein said insert member has an opening shaped to receive said actuator member.

8. The kit of claim 1 wherein said dispenser housing further comprises a holding chamber in fluid communication with said orifice.

9. The kit of claim 1 wherein dispenser housing further comprises a mouthpiece in fluid communication with said orifice.

10. The kit of claim 1 wherein said dispenser housing comprises a pair of laterally extending wings adapted to be gripped by a user.

11. The kit of claim 1 wherein said insert member is connected to said dispenser housing with a tether.

12. The kit of claim 1 further comprising a plug removeably received in said insert member.

13. The kit of claim 12 wherein said plug is connected to said dispenser housing with a tether.

14. The kit of claim 1 wherein said first and second container assemblies each hold a medicament.

15. The kit of claim 1 wherein said peripheral wall comprises an opening therein adjacent said support block.

16. A medication delivery device comprising:
a dispenser housing comprising a support block having a well and an orifice communicating with said well, said dispenser housing comprising a first peripheral wall defining a cavity, wherein said dispenser housing comprises an upright member extending interiorly within said cavity;
an insert member disposed in said cavity of said dispenser housing, said insert member having a second peripheral wall nesting with said first peripheral wall, and a floor defining an interior space, wherein said floor has a first opening aligned with said well of said dispenser housing and a second opening laterally spaced from said first opening, wherein said upright member extends through said second opening;
a medicament container comprising a canister and a valve stem extending through said opening in said floor and received in said well in said support block, wherein said canister is reciprocally moveable relative to said valve stem along a longitudinal axis defined by said valve stem; and
a plug removeably received in said insert member.

17. The medication delivery device of claim 16 wherein said insert member is mounted to said dispenser housing with a snap fit.

18. The medication delivery device of claim 16 wherein said insert member has a peripheral rim extending outwardly from said peripheral wall along a free edge thereof.

19. The medication delivery device of claim 16 wherein said dispenser housing further comprises a holding chamber in fluid communication with said orifice.

20. The medication delivery device of claim 16 wherein dispenser housing further comprises a mouthpiece in fluid communication with said orifice.

21. The medication delivery device of claim 16 wherein said dispenser housing comprises a pair of laterally extending wings adapted to be gripped by a user.

22. The medication delivery device of claim 16 wherein said insert member is connected to said dispenser housing with a tether.

23. The medication delivery device of claim 16 wherein said plug is connected to said dispenser housing with a tether.

24. A ventilator system comprising:
a dispenser housing in fluid communication with an oxygen intake line and a patient interface, said dispenser housing comprising a support block having a well and an orifice communicating with said well, said dispenser housing comprising a peripheral wall defining a cavity, and an upright member extending interiorly within said cavity;
an insert member adapted for releasable mounting to said dispenser housing in said cavity and defining an interior space, said insert member having a floor with a first opening adapted to be aligned with said well of said dispenser housing when said insert member is mounted to said dispenser housing and a second opening laterally spaced from said first opening, wherein said upright member extends through said second opening; and
a plug removeably received in said insert member.

25. The ventilator system of claim 24 further comprising a first container assembly comprising a valve stem shaped to be received by said well in said support block, said first container assembly shaped to be disposed in said interior space of said insert member.

26. The ventilator system of claim 25 wherein said first container assembly holds a medicament.

27. The ventilator system of claim 24 wherein said dispenser housing comprises a pair of laterally extending wings adapted to be gripped by a user.

28. The ventilator system of claim 24 wherein said insert member is connected to said dispenser housing with a tether.

29. The ventilator system of claim 24 wherein said plug is connected to said dispenser housing with a tether.

30. The ventilator system of claim 24 wherein said peripheral wall comprises an opening therein adjacent said support block.

31. A kit for assembling different configurations of a medication delivery device comprising:
   an insert member comprising a first peripheral wall defining a first cavity adapted and shaped to receive a pressurized metered dose inhaler comprising a valve stem; and
   a dispenser housing comprising a support block having a well and an orifice communicating with said well, said dispenser housing comprising a second peripheral wall defining a second cavity having a larger volume than said first cavity, wherein said second cavity is adapted and shaped to receive either said pressurized metered dose inhaler configured with a dosage counter, wherein said valve stem is received in said support block, or said insert member with said pressurized metered dose inhaler inserted into said first cavity of said insert member, wherein said valve stem is received in said support block, and wherein said pressurized metered dose inhaler configured with a dosage counter in combination with said insert member is not adapted to be mounted in said second cavity of said dispenser housing.

32. The kit of claim 31 wherein said insert member comprises a floor having an opening therethrough, wherein said opening is aligned with said well when said insert member is mounted in said dispenser housing.

33. The kit of claim 31 wherein said dispenser housing comprises an actuator member adapted to interface with the dose counter.

34. The kit of claim 33 wherein said actuator member comprises an upright finger.

35. The kit of claim 34 wherein said insert member has an opening shaped to receive said actuator member.

36. The kit of claim 31 wherein said dispenser housing further comprises a holding chamber in fluid communication with said orifice.

37. The kit of claim 31 wherein dispenser housing further comprises a mouthpiece in fluid communication with said orifice.

38. The kit of claim 31 wherein said insert member is connected to said dispenser housing with a tether.

39. The kit of claim 31 further comprising a plug removeably received in said insert member.

40. The kit of claim 39 wherein said plug is connected to said dispenser housing with a tether.

41. The kit of claim 31 wherein said pressurized metered dose inhaler comprises a medicament.

* * * * *